United States Patent [19]

Lillig et al.

[11] 4,322,216

[45] Mar. 30, 1982

[54] METHOD AND APPARATUS FOR POSITIONING CARS IN A SAMPLE HANDLING APPARATUS

[75] Inventors: John E. Lillig, Diamond Bar; Robert K. Neeper, Yorba Linda; Paul J. Ashton, Riverside, all of Calif.

[73] Assignee: Beckman Instruments, Inc., Fullerton, Calif.

[21] Appl. No.: 238,306

[22] Filed: Feb. 26, 1981

[51] Int. Cl.³ .......................... G01N 1/10; G01N 1/14
[52] U.S. Cl. ............................... 23/230 R; 73/864.25;
422/64; 422/65; 422/67; 422/100
[58] Field of Search ................ 23/230 R; 422/64, 65,
422/67, 100; 73/423 A; 364/497; 235/475;
141/130

[56] References Cited

U.S. PATENT DOCUMENTS

| | | | |
|---|---|---|---|
| 3,687,632 | 8/1972 | Natelson | 23/259 |
| 4,011,048 | 3/1977 | Johnson, Jr. et al. | 23/259 |
| 4,058,367 | 11/1977 | Gilford | 23/253 |
| 4,157,871 | 6/1979 | Anderson et al. | 23/230 B |
| 4,259,290 | 3/1981 | Suovaniemi | 422/67 X |
| 4,268,477 | 5/1981 | Herzstark | 422/64 |

Primary Examiner—Ronald Serwin
Attorney, Agent, or Firm—R. J. Steinmeyer; J. E. Vanderburgh; Timothy R. Schulte

[57] ABSTRACT

A method and apparatus for conveying liquids to and from a reaction cell in an automated sample handling apparatus. The conveyance apparatus includes a track and car system. A method and apparatus is disclosed which precisely positions the cars on the track. This positioning method and apparatus includes a plurality of apertures and spaces on the track of a size and spacing to allow the cars to accurately position themselves.

8 Claims, 6 Drawing Figures

METHOD AND APPARATUS FOR POSITIONING CARS IN A SAMPLE HANDLING APPARATUS

BACKGROUND OF THE INVENTION

1. Field of the Invention

The invention relates to the field of automated conveyance. More particularly the invention relates to a positioning method and apparatus. In still greater particularity, the invention relates to a track and car system utilizing a combination of apertures and spaces on a rail to accurately position a plurality of automated cars.

2. Description of the Related Art

Many measuring and testing instruments, as for example, immunonephelometric instruments, such as that described in U.S. Pat. No. 4,157,871 issued on June 12, 1979, and incorporated herein by reference, require successive manipulations of a sample substance to be tested. In addition, pending application U.S. S.N. 141,455 discloses other details of this system and is incorporated by reference. That application is assigned to the same assignee as this application and the above U.S. Patent. These manipulations consume a great deal of operator time when a number of assays on many samples are performed. To obtain good results, an operator must repeat a number of steps in the proper sequence for each sample. Manual pipetting steps include the identification of a number of samples as well as numerous sample dilutions. Because the sample manipulations are usually done manually, operator fatigue and boredom often result in erroneous results. Additionally, reduced operator morale due to fatigue and boredom generally contributes to a decrease in job performance resulting in increased operating costs for the laboratory. Also, manual manipulations consume a great deal of time often resulting in long delays to obtain results.

Automated sample handling systems have been used to replace the manual sample manipulations previously relied on. In such systems, one or more automated cars or robots are employed. One problem with these systems is the positioning of the robots to perform the operations. That is, exact positioning of the robots to allow access of a pipette to a sample cup or other container is difficult to achieve. The precision required results in the use of expensive sensors and costly systems. In addition, the systems have been subject to errors should the robots get lost on the track. Thus continual monitoring and repositioning of a car has been required with prior systems. Errors may also be introduced into the system by interference such as dirt or scratches on the track. That is, where apertures are used on the track as position determinations, dirt or other foreign material may interfere with the apertures. These problems are especially acute where narrow apertures are used in precise positioning apparatus. When, as with most systems, counting is used, the nondetection of an aperture will result in the robot stopping at the wrong aperture. This error will carry through and will result in continually incorrect results. In addition, should a robot in one of the systems be bumped or otherwise interfered with, the system would have to be shut down and the cars manually repositioned to ensure accuracy. It would be desirable to have a robot positioning system which would be "smart" enough to know its position and which could verify its position continuously to ensure that each car remains accurately positioned.

The above problems are especially acute in an automated sample handling system utilized by an automated clinical diagnostic instrument. In such a system the cars move back and forth along the track and the cars must cover relatively large distances accurately. Because incorrect positioning could yield an incorrect result, possibly resulting in a wrong diagnosis for a patient, these cars must recognize their relative position on the guide track at all times.

SUMMARY OF THE INVENTION

The invention is an automated sample handling apparatus to be used with a testing instrument. The device includes a sample containment apparatus which cooperates with an automated pipetting system to provide easy and quick access to the sample substance and other substances as necessary. The automated apparatus transports the sample substance and reagents to and from the reaction cell in the testing instrument.

Transporting apparatus is provided in the automated sample handling system for conveying the substances to and from the diluting and reaction areas. The transporting apparatus includes a track and at least one robot or car mounted on the track. Preferably, three cars are used: one to transfer the sample to the diluting well; one to transfer the diluted sample to the reaction cell; and one to transfer the reagent to the reaction cell. Because precise positioning of the cars on the track is important, a positioning apparatus includes optical sensors mounted on the cars. These sensors detect reflected light from the track and identify apertures which are located at predetermined points on the track. Each car is modular, self-contained, and easily detached from the rail for service or replacement. The automated pipette assembly or each car may be slightly different but all are mounted on the car assembly in an identical manner.

DESCRIPTION OF THE PREFERRED EMBODIMENT

Figure 1:
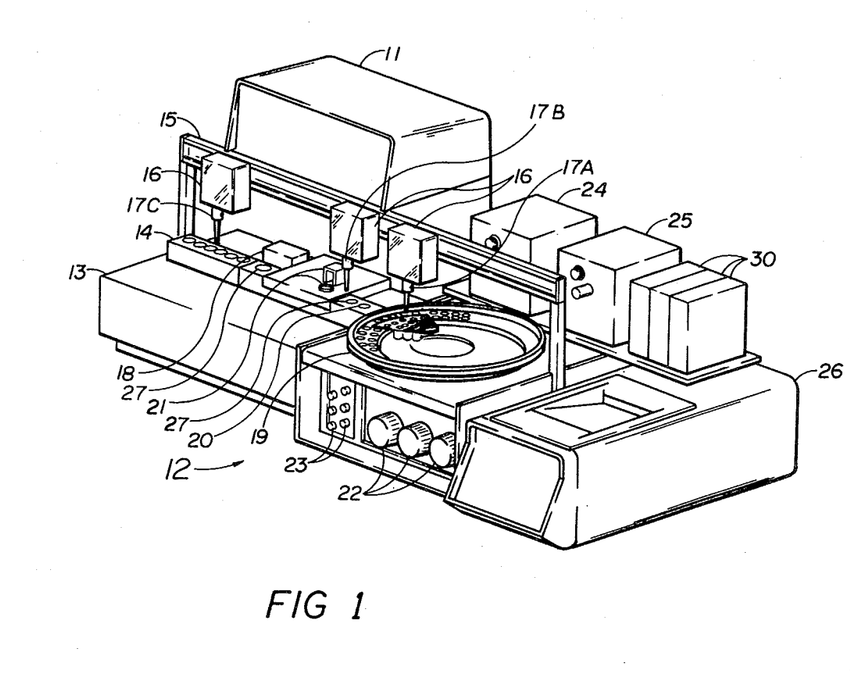
FIG. 1 is an overall perspective view of the automated sample handling apparatus in accordance with the present invention.

A better understanding of the invention may be had by referring to the drawing wherein like reference numerals denote like structure throughout each of the various figures. Referring to FIG. 1, a testing instrument 11 which may include a nephelometer is positioned adjacent an automated sample handling apparatus generally designated 12. Automated sample handling apparatus 12 includes a base 13 and a reagent bottle holder 14. A remotely controlled transporting means includes a movable car or cars 16 mounted on a track 15 which defines a traveling path therefor. Track 15 is mounted on base 13. An automated pipette 17A, B or C is mounted on each of cars 16.

A containing means which includes a turntable 19, is rotatably mounted on base 13 to allow automated pipette 17A or B access thereto. A card reader 18 and reaction cell 21 are mounted on base 13. Reaction cell 21 includes a flip-up cover. Antigen excess dilution wells 20 are mounted adjacent turntable 19. Peristaltic pumps 22 and fluid control valves 23 are also mounted on base 13. A source of diluent which may include a fixed ratio diluter 24 is mounted on base 13 adjacent turntable 19. A buffer dispenser 25 is mounted adjacent fixed ratio diluter 24. A data processor 26 is positioned adjacent the automated sample handling apparatus 12. Pipette wash stations 27 are mounted on base 13. A plurality of containers 30 containing diluent or other liquids are positioned adjacent diluter 24 and dispenser 25 and may be plumbed thereto.

Figure 2:
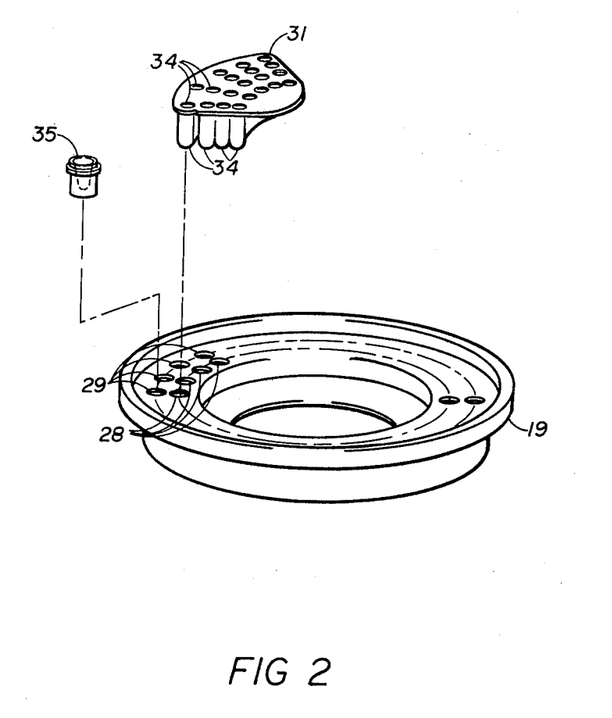
FIG. 2 is a perspective view of the turntable and removable tray.

Referring to FIG. 2, a containing means includes turntable 19 having an inner and outer concentric row of holes 28 and 29, respectively. A removable tray section 31 includes a plurality of wells 34. Wells 34 are open at the top of tray 31 to allow automated pipette access thereto. Wells 34 extend downwardly and are spaced apart to define a series of rows with a first row at the narrow innermost width portion of tray section 31 and a last row configured in a wider arc at a wide outermost width portion of removable tray section 31. The portions of wells 34 in the last row which extends downwardly from tray section 31 are spaced from the next to last row and from each other to allow each of these portions to be inserted into a hole in inner row of holes 28 as illustrated by the broken line in FIG. 2. A sample container 35 is insertible into outer row 29.

Figure 3:
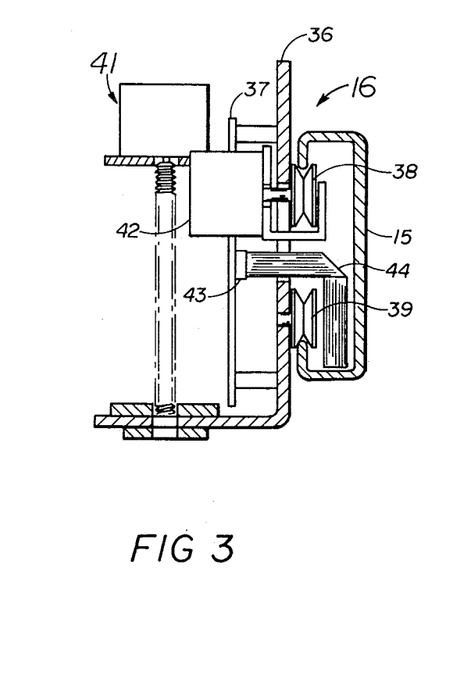
FIG. 3 is a partially sectioned side view of the track and car apparatus.

Referring to FIG. 3, a partially sectioned side view of the remotely controlled transporting apparatus is shown. Car 16 is mounted on track 15 and includes an L-shaped bracket 36 to support the component parts. Mounted on the vertical leg of L-shaped bracket 36 is a control board 37 containing all the necessary electronic circuitry to drive the associated apparatus. An upper wheel 38 and a pair of lower wheels 39 (only one shown) are mounted on the rear face of the vertical leg of L-shaped bracket 36. Upper wheel 38 and lower wheels 39 engage track 15. Lower wheels 39 are rotatably mounted on L-shaped bracket 36 while upper wheel 38 is part of a spring loaded assembly for horizontal drive. An elevator assembly 41 for vertical drive is mounted on a lower leg of L-shaped bracket 36. An automated pipette (not shown) attaches to elevator assembly 41. A stepper motor 42 drives upper wheel 38. Electrical power and control signals are supplied to control board 37 through a connector 43 and ribbon cable 44.

Figure 4:
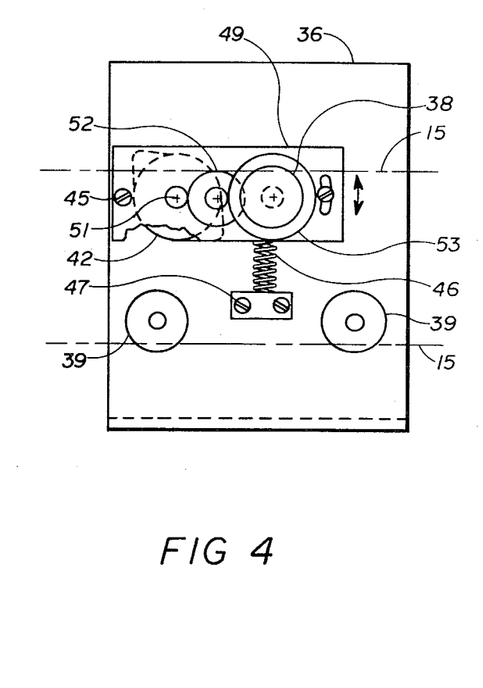
FIG. 4 shows a rear view of the horizontal car drive assembly.

Referring to FIG. 4, the horizontal drive assembly is shown as viewed from the rear. The assembly is mounted to L-shaped bracket 36 by a pivot 45 and is free to rotate in the direction indicated by the arrows. A spring 46 and a spring block 47 apply an upward force to the assembly. When lower wheels 39 are engaged with the lower lip of track 15, upper wheel 38 is wedged onto an upper lip of track 15. As upper wheel 38 is driven, the car travels along track 15. The drive is assembled to a drive bracket 49. The drive includes a stepper motor 42 and a pinion 51. An intermediate cluster gear 52 communicates between motor pinion 51 and a wheel gear 53 on wheel 38. The gear ratio from pinion 51 to the wheel is preferably 25:1. This gear ratio gives a fine motion resolution and amplifies the driving torque supplied by motor 42.

Figure 5:
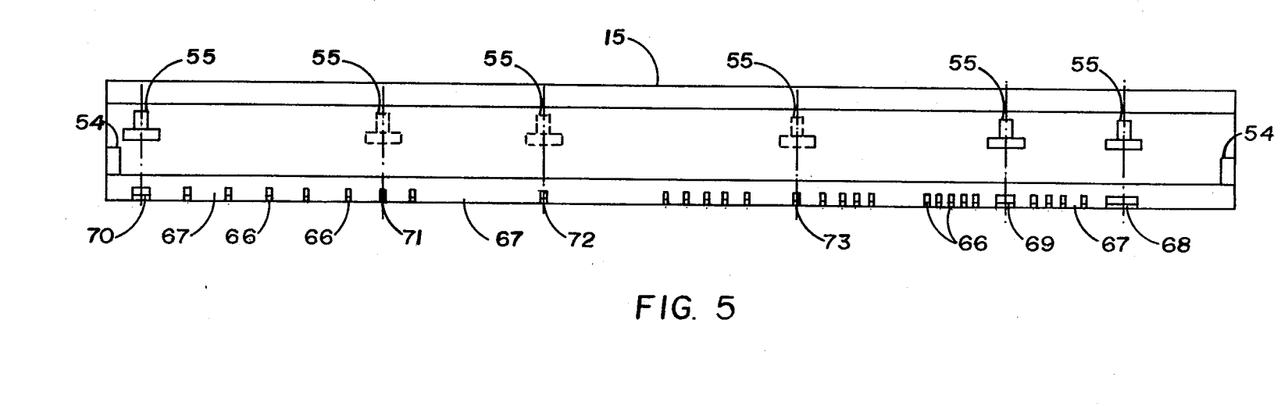
FIG. 5 shows the car positioning apparatus.

Referring to FIG. 5, a car positioning means includes a plurality of apertures 66 and 68–73 in track 15. A plurality of spaces 67 are provided between the apertures. A stop 54 is mounted at each end of track 15. An optical sensor 55 is mounted on control board 37 of each car (shown in FIG. 3).

Figure 6:
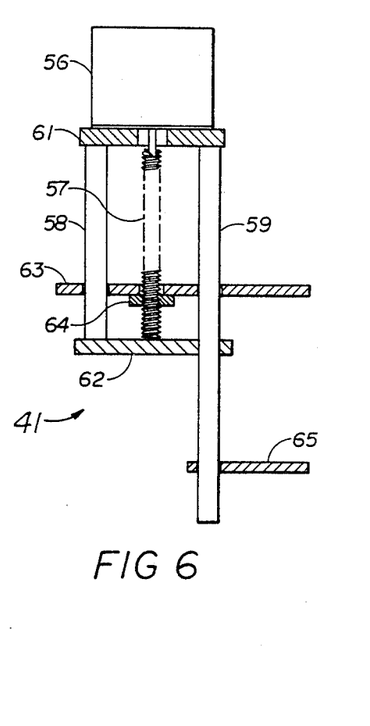
FIG. 6 shows the elevator mechanism for the automated pipette.

Referring to FIG. 6, elevator mechanism 41 is shown in detail. A stepper motor 56 has a lead screw 57 welded to its shaft. A support rod 58 and guide rod 59 separate a motor mount plate 61 from an assembly mount plate 62. A pipette mount plate 63 is journaled to slide freely up and down guide rod 59. A slot (not shown) engages support rod 58 preventing rotational freedom of plate 63. Mounted on plate 63 is a floating nut 64 which engages lead screw 57. Although not essential floating nut 64 is utilized to avoid high torque load due to binding, as small eccentricities exist with reasonable manufacturing tolerances. A lower pipette guide plate 65 establishes the position of the automated pipette.

Mode of Operation

Referring to FIG. 1, base 13 is positioned adjacent nephelometer 11. Reaction cell 21 is the measuring site for nephelometer 11. Reaction cell 21, turntable 19, wash stations 27 and reagent bottle holder 14 are positioned along a path allowing automated pipettes 17 to access each location while traveling along track 15. While track 15 is shown as a straight line in the preferred embodiment, it should be understood that track 15 may be curved or angled or otherwise nonlinear.

The distance between reaction cell 21 and turntable 19 is known. Similarly, the distances between turntable 19 and other locations in the automated system are known. The vertical height of these locations is fixed such that they are all at approximately the same level. Thus, track 15 is suspended above base 13 a fixed distance therefrom to allow automated pipettes 17 on cars 16 to accurately travel the distance necessary to access the substances in locations such as reagent bottle holder 14, wash stations 27, reaction cell 21 and turntable 19.

Peristaltic pumps 22 provide rinse solutions to reaction cell 21 or automated pipettes 17 depending upon the state of fluid control valves 23. Fluid control valves 23 direct fluid flow by "pinching" off all the fluid lines except the one where fluid is required. Fluid is pushed through this line by a peristaltic pump 22 or buffer dispenser 25.

Automated sample handling system 12 is controlled by data processor 26. Data processor 26 contains a 24 digit alphanumeric display, printer, keyboard, and cassette program loader. The system program can be easily changed, by reading a new cassette, to several modes of operation. The operator interfaces with the system via the keyboard by responding to program questions. The operator sets up the assay, presses start and the instrument will perform the required motions to obtain and print out results. Because the system is automated, human error, which resulted from manual manipulation, is eliminated thus allowing for more accurate results. The automated system also allows the results to be obtained more quickly than with manual systems. All that is required of the operator is that he load the proper cassette into data processor 26. The data processor 26 prompts the operator to read from one to six antibody cards using card reader 18 and position antibody bottles in reagent rack 14. Following the last antibody card entry, data processor 26 prompts the reading of the calibrators until a calibrator is available for each assay being run. The operator then enters the turntable positions where the samples to be assayed are located along with the antibody bottle locations to identify which assays are to be run. The printer then prints a summary of the inputs and directs placement of any reagents needed. If no operator programming changes are required, the operator presses start and leaves the instrument.

The operation of the automated sample handling system results first in a cleaning of reaction cell 21 and priming of all input fluid lines and pipettes 17 with liquid. Dilutions of samples may be made using automated pipette 17A. Turntable 19 rotates such that pipette 17A can access the sample substance in one of the appropriate sample cups 35 (FIG. 2) located in one of the apertures in the outside ring 29 on turntable 19. Pipette 17A moves into position and lowers the pipette tip into the sample substance. The required amount of sample is drawn up into the pipette tip. Diluter pipette 17A is pulled up out of sample cup 35 (FIG. 2) and car 16 moves it over a dilution well 34 in removable tray section 31. This dilution well 34 is preferably in the outermost row of wells 34. Diluter pipette 17A is lowered into well 34 and the sample is delivered. Diluent is supplied to well 34 either from diluter 24 plumbed into pipette 17A or by other conventional means. Mixing of the sample and diluent is then accomplished by conventional apparatus such as by magnetic stir bars.

Following the last dilution of a particular sample, automated pipette 17B moves to a position over one of the wells 34 in the narrow row portion of removable tray section 31. Once in position automated pipette 17B lowers into well 34 and draws up the finally diluted sample. Automated pipette 17B then moves on track 15 to a position over reaction cell 21. Automated pipette 17B lowers and delivers the required amount of diluted sample into reaction cell 21 and moves to one of wash stations 27. A similar procedure is followed by automated pipette 17C which delivers the required amount of reagent from reagent bottle holder 14 to reaction cell 21. The timing is such that the antibody or reagent is delivered within seconds of the sample delivery.

Referring to FIG. 3, cars 16 ride on track 15. The power to drive cars 16 is supplied through ribbon cables 44. Attached to each of ribbon cables 44 is a fluid line which connects with the automated pipette 17 mounted on each car 16. Ribbon cables 44 roll and unroll as cars 16 traverse track 15 horizontally. Ribbon cables 44 nest and pass by each other allowing nearly full travel for each car 16 from end to end of track 15.

In order to allow cars 16 to move on the same track 15, a positioning means is provided whereby each car can recognize designated positions on track 15 including a "home" position. The positioning means includes apertures 66, spaces 67, apertures 68–73 and optical sensors 55. Apertures 66 and 68–73 are spaced along the lower lip of track 15. Reflective optical sensors 55 mounted on control board 37 sense reflected light from the track lip. While an infrared optical sensor is utilized in the preferred embodiment, any optical or mechanical sensor may be employed without departing from the scope of the invention. When sensors 55 detect the metal of track 15, the signal is high. When apertures are encountered, the signal is low because the light is no longer reflected from track 15.

The "home" position is important because, when multiple cars are used, it allows them to find their travelling area on the track. It thus provides a reference point and helps to prevent lost cars. Lost cars could occur if the operator mispositions a car on the track or if a car is bumped. For each subsequent measurement each car will pass through its home position and all aperture counts per sequence must match a pre-defined number to ensure proper car travel. To find its respective home position each car is set in motion and compares incoming aperture information to a map in the system memory until it recognizes its position on track 15. This is accomplished by relative timing between aperture measurements. The car is then directed to its home position.

Referring to FIG. 5, track 15 includes fixed stops 54 on either end of it, which prevent the cars from moving off the ends of track 15. By placing large apertures 68 and 70 on ends of the track, the two outer cars (with pipettes 17A and 17C), after being driven to the extreme edges, will stop at the edges, knowing that they are now in a known position at the extreme edges of the track. The middle car (pipette 17B) also has a large aperture 69 to reference its initial position. This hole is slightly smaller than the apertures at the edge of the track, so the right hand car will not detect it as its referencing position. This aperture is positioned so the middle car will be on the hole if both the right and middle cars are moved to the far right-hand side of the track. These positions adjacent the ends of the track are defined as reference positions for the cars.

From these reference positions the cars may then be moved and the track may be verified for damage or other markings (dirt, scrapes, etc.) that may cause failure in the system operation. All cars are thus directed to move away from the edges toward the center of the track 15. Limits are set for their movement. These limits are the maximum distance the cars will be allowed to be moved, before an error is indicated. These limits are defined in terms of a maximum number of steps of stepper motor 42.

During the movement of the cars away from the edges of track 15, the number of apertures and spaces passed is recorded by data processor 26.

While any of the cars are moving, the following tests are done (for each of the three cars) at each step of stepper motor 42:

1. Sensor test if on or off an aperture.
2. If off an aperture, then proceed to step 6.
3. Add 1 to the step count.
4. If the step count equals 15, then indicate that an aperture has been found. (In the preferred embodiment all apertures except the reference apertures are 30 steps wide.)
5. Set the space count to 0 and return to step 1.
6. Set the step count to 0.
7. If an aperture was found (in step 4 above) then add 1 to the number of apertures found.
8. Add 1 to the space count. (The space count is defined as the width of a space in terms of steps of the stepper rotor.)
9. If the space count exceeds a predetermined space count then stop the car and indicate that a valid stop has occurred. If the space count was not exceeded, then return to step 1.

There is a maximum space count for each car which signals the upcoming home position. That is, the car with pipette 17C must encounter one space which is larger than 450 steps before stopping. This is the space to the left of aperture 72. The car with pipette 17B must encounter one 450-step space before stopping. This is the space to the right of aperture 72. The right car with pipette 17A must encounter two 300-step spaces before stopping. That is, car 17C will stop on the space to the left of aperture 72, car 17B will stop in the space just to the right of aperture 72, and car 17A will stop in the space to the left of aperture 73.

After all of the cars have come to a stop, the number of apertures found by each car is checked against a predetermined number. If the number of apertures found differs from the predetermined number, then it is assumed that there is an error in either the track or the car, and an error is indicated specifying which car is in error. An error is also indicated if any of the cars passed its maximum space count in the track. The cars and the track have now been verified, and the cars are moved to their respective home positions by moving the left car to the left two apertures to aperture 71. The middle car 17B is moved to the left to aperture 72. The right car 17A is moved to the right one aperture to aperture 73. The cars are now at their home positions. The reference positions for the three cars are indicated by the solid sensors 55 in FIG. 5 while the home positions are indicated by the broken line sensors 55 in FIG. 5.

With the cars in known positions, it is now possible for them to move left or right several apertures, without getting confused as to their relative position on the track. The three cars may pass over some of the same apertures during their movements. For example:

Left car's basic cycle:
1. Move left to the aperture 70 at the left end of the track verifying that six holes are found.
2. Move right to desired hole.
3. Get solution from bottle located at this position.
4. Move to the right, back to its home position (aperture 71).
5. Move right to the large space, verifying that one aperture is found.
6. Move to the right one aperture, and dispense solution.
7. Move back to the left two apertures (back to home).

Middle car's basic cycle:
1. Move right to medium space (300 steps wide).
2. Verify that four apertures were passed.
3. Move right to medium-sized space (300 steps wide).
4. Verify that five apertures were passed over.
5. Move left to desired aperture, and get solution.
6. Move to large space (450 steps wide) and verify number of apertures passed over.
7. Dispense solution.
8. Move back to home (one aperture to the right).

Right car's basic cycle:
1. Move to right two apertures to move out of the way for the middle car.
2. Move to the left until a medium-sized space is found and verify that seven apertures were found.
3. Move to the left until a second medium-sized space is found (300 steps wide).
4. Pick up solution.
5. Move to the right one aperture at a time, as required.
6. Move right to a large aperture verifying that the correct number of apertures are found.

Thus, the real position of the car is checked at least twice on each cycle of the car movement. If the car should fail one of the verification steps, an error would be indicated, specifying which car has failed in its movement.

In the preferred embodiment, the width of all apertures except the reference position apertures was chosen to be 30 steps of stepper motor 42. This width is large enough to eliminate the possibility of a scratch on track 15 appearing as one of the apertures. Also, it is wide enough to ensure aperture detection even if an aperture is partly blocked due to dirt on a raised edge on the aperture or misadjusted sensors. Exact stopping position within an aperture is determined by reflectively sensing the edge of the aperture, counting out 15 steps, and then halting. This procedure provides an excellent stop position resolution.

Thus, an extremely accurate positioning method and apparatus are disclosed which ensures that no errors will occur in positioning of the cars. This is especially important in clinical instruments where accuracy is required for correct diagnosis. Thus, dilutions on turntable 19, the correct picking up of reagents from holder 14, access to dilution well 20, wash station 27, and reaction cell 21 may be accurately and reliably performed.

Referring to FIG. 6, the vertical position of automated pipette 17 is established by lead screw 57 and the step ratio of stepper motor 56. To avoid requiring position sensors, pipette mount plate 63 is driven downward against a hard stop 62 and stepper motor 56 is stepped additionally. When the direction is reversed, the beginning position is thus established by hard stop 62. The vertical position can never get lost since overstepping will result in pipette mount plate 63 contacting hard stop 62.

Advantages of the automated sample handling system include the ability to dilute a sample with either of two reagents and deliver a specific volume of that diluted sample to reaction cell 21. The system may also deliver a number of other reagents to reaction cell 21 depending upon the assay to be performed. Protein assays require only one more component, the antibody, while drug assays require drug conjugated to protein and antibody to be delivered. Hence, the sequence is modified from the protein sequence when drugs are assayed. The use of a data processor 26 to control the system sequence and interface with the operator allows minimal operator effort to set up the test sequence and unattended operation once the test sequence is established. Car 16 and track 15 are designed to be small, compact, and low cost. Motion control is accomplished with circuitry and programmed software through data processor 26. Complex functions are therefore performed by relatively simple mechanical design. The shapes, sizes, and extensions of this design can be modified for any desired application. The increased efficiency achieved by the invention reduces lead times and allows more accurate results in a shorter time.

Antigen excess dilution wells 20 are fixed and do not rotate with turntable 19. Dilutions of calibrator substance may be made into these cups to provide antigen excess checking solutions for those assays requiring antigen excess determination. Prediluting into these wells minimizes excess manipulation and increases efficiency by eliminating timing conflicts in cars 16 carrying sample to reaction cell 21.

While particular forms of the invention have been disclosed with respect to a preferred embodiment thereof, it is not to be so limited as changes and modifications may be made without departing from the scope of the invention. For example, while the invention has been disclosed as employed with a nephelometer, it may be advantageously employed with other testing apparatus. Any testing apparatus requiring handling and manipulations of a sample substance could advantageously employ this invention. In addition, turntable 19 could be replaced by a series of trays which move in alternate patterns. Track 15 need not be limited to a straight line configuration but could in fact be curved or angled. While three cars 16 are used in the preferred embodiment, the invention could be utilized with other than three cars.

The foregoing description, taken together with the appended claims, constitutes a disclosure which enables one skilled in the art and having the benefit of the teachings contained therein to make and use the invention. Further, the structure herein described constitutes a meritorious advance in the art which is unobvious to such skilled workers not having the benefit of these teachings.

What is claimed is:

1. A positioning apparatus for an automated sample handling system including a track for guiding the movement of a plurality of automated cars movably mounted on said track, said cars driven by a stepper motor on each said car, said positioning apparatus comprising:
   a rail portion;
   a plurality of apertures on said rail, at least some of said apertures being of different sizes and spaced apart different distances;
   means, mounted on each said car, for sensing said rail and said apertures; and
   means, connected to said sensing means, for counting said steps of said stepper motor as said car moves past said apertures and said spaces, said counting means also counting the number of apertures passed by said moving car.

2. A method for positioning a plurality of cars on a single track, each said car driven by a stepper motor, said track terminating in two ends and including a plurality of apertures between said ends, at least some of said apertures being of predetermined different width and having predetermined different sized spaces between said apertures, said method comprising the steps of:
   advancing each said car to its reference position adjacent said ends;
   driving said cars away from said ends;
   sensing said apertures and said spaces on said track simultaneously with said step of driving;
   counting said apertures and said steps of said stepper motor simultaneously with said step of sensing; and
   stopping each said car at a predetermined position determined by the number of apertures and spaces passed and the number of steps counted.

3. Method according to claim 2 wherein said step of stopping includes comparing said number of apertures counted against a predetermined aperture count for each said car.

4. Method according to claim 2 further including the step of moving said cars a predetermined number of apertures to a home position.

5. Method according to claim 2 further including the step of moving said cars a predetermined number of apertures to a desired position.

6. Method according to claim 5 further including the step of verifying the position of said cars.

7. Method according to claim 2 wherein said step of stopping includes indicating an error if the number and size of said apertures and spaces passed are not equal to predetermined reference numbers.

8. Method according to claim 2 further including the step of counting the number of steps after detecting an aperture and comparing that number to a number based on one-half the width of the narrowest aperture on the track as measured in steps of the stepper motor.

* * * * *